US005154888A

United States Patent [19]

Zander et al.

[11] Patent Number: 5,154,888

[45] Date of Patent: Oct. 13, 1992

[54] AUTOMATIC SEALING CLOSURE MEANS FOR CLOSING OFF A PASSAGE IN A FLEXIBLE CUVETTE

[75] Inventors: Dennis R. Zander, Penfield; John B. Chemelli; Craig A. Caprio, both of Rochester, all of N.Y.

[73] Assignee: Eastman Kodak Company, Rochester, N.Y.

[21] Appl. No.: 776,955

[22] Filed: Oct. 15, 1991

Related U.S. Application Data

[63] Continuation-in-part of Ser. No. 603,596, Oct. 25, 1990, abandoned.

[51] Int. Cl.[5] .......... G01N 21/03

[52] U.S. Cl. .......... 422/58; 422/61; 422/102; 422/103; 436/165; 436/180; 436/808; 435/287; 435/301; 206/219; 383/66

[58] Field of Search .......... 422/55, 58, 61, 102, 422/103; 435/165, 180, 808; 436/287, 300, 301; 206/219; 383/66, 84

[56] References Cited

U.S. PATENT DOCUMENTS

| | | | |
|---|---|---|---|
| 3,036,894 | 5/1962 | Forestiere | 422/61 X |
| 3,476,515 | 11/1969 | Johnson et al. | 436/165 |
| 3,713,779 | 1/1973 | Sirago et al. | 436/165 X |
| 4,007,010 | 2/1977 | Woodbridge, III | 422/58 X |
| 4,065,263 | 12/1977 | Woodbridge, III | 422/57 |
| 4,673,657 | 6/1987 | Christian | 435/301 X |
| 4,795,265 | 1/1989 | Dahlberg et al. | 206/219 X |
| 4,965,047 | 10/1990 | Hammond | 422/61 X |
| 4,985,204 | 9/1991 | Klose et al. | 422/58 X |

FOREIGN PATENT DOCUMENTS 0381501 8/1990 European Pat. Off. .

*Primary Examiner*—Lynn M. Kummert
*Attorney, Agent, or Firm*—Dana M. Schmidt

[57] ABSTRACT

There are described a cuvette and a method for sealing off flow such as flow in a passageway from an access port in the cuvette with a closure, that ensures a complete seal merely by applying the closure. The cuvette is improved in that it has the closure in a closure portion that is joined to the rest of the cuvette along a hinge line that passes through the passageway to be closed off, so that application of the closure by bending the closure portion about the hinge line pinches off the passageway.

7 Claims, 7 Drawing Sheets

110F
200F
190F
122F
310
184F
121F 400
420

110G
26G
121G
44G
46G
XIV
XIV
184G
190G
40G
198G 400
420
26G
190G
410
110G
184G
412

210H
110H
122H
506
508
200H
184H
26H
14H
502
121H
500
190H 60I
14I
26I
190I
122I
12I
110I
184I
510
200I
512

500
121H
502
504

AUTOMATIC SEALING CLOSURE MEANS FOR CLOSING OFF A PASSAGE IN A FLEXIBLE CUVETTE

RELATED APPLICATIONS

This application is a continuation-in-part of U.S. Ser. No. 603,596 filed on Oct. 25, 1990, now abandoned.

FIELD OF THE INVENTION

The invention relates to a cuvette for doing reactions, preferably while completely confined against leakage, and particularly to an improved closure for an access port of the cuvette.

BACKGROUND OF THE INVENTION

EPA Publication No. 381,501, commonly-owned with this application, describes a containment cuvette that is presupplied and sealed with the reagents necessary to detect selected nucleic acids that are multiplied in the cuvette. In addition, a patient's sample is injected through a port, which port is then sealed such as by heat-sealing the plastic around the port or inserting a stopper. As a result, a complete containment occurs, even through the detection stage, so that there is no risk of any multiplied nucleic acid (hereinafter, "amplified" nucleic acid) from straying from the cuvette as an aerosol to contaminate yet-to-be used cuvettes.

Such a cuvette has been very effective in testing for DNA, by allowing PCR amplification to be done safely and without contamination. However, a minor drawback exists in that the patient sample port has to be carefully sealed to ensure nucleic acid does not leak out. Whether or not heat-sealing or a mechanical stopper is used, in either case, care must be exercised as otherwise a complete seal may not occur.

Still further, other, temporary seals of the cuvette have not always held as desired.

Therefore, there has been a need prior to this invention for a method, and for features in a flexible cuvette, that allow for automatic closure of passageways such as that extending from the patient sample port after sample insertion, without requiring special care.

SUMMARY OF THE INVENTION

I have constructed closure means that solve the aforementioned problem.

More specifically, in accord with one aspect of the invention, there is provided a flexible cuvette defined by opposed flexible sheets sealed together to define at least one compartment between them for holding a liquid, and a passageway leading to or from the one compartment;

the improvement wherein the cuvette further includes means for sealing off flow through the passageway, the means comprising a fold line extending across the passageway at at least one location, so that the cuvette can be folded about the hinge line sufficiently to pinch off flow through the passageway, and further including means for retaining the folded condition for as long as necessary.

In accord with another aspect of the invention, there is provided a method for sealing off flow through a passageway in a flexible cuvette to or from a compartment, the method comprising a) providing a fold line extending across the passageway at least once, b) folding the cuvette about the fold line so as to pinch off flow through the passageway, and c) holding the cuvette folded as set forth in step b) for as long as flow is to be sealed off through the passageway.

Therefore, it is an advantageous feature of the invention that the access port of a cuvette is easily sealed off simply by attaching the cover that is an integral part of the cuvette.

It is a related advantageous feature of the invention that such sealing as described above does not rely solely on the cover that fits over the access port, but on a pinching effect created in the act of applying the cover.

Other advantageous features will become apparent upon reference to the following "Description of the Preferred Embodiments", when read in light of the attached drawings.

DESCRIPTION OF THE PREFERRED EMBODIMENTS

The invention is described for preferred embodiments in which nucleic acid is amplified and detected while completely contained, to prevent contamination, such as by using PCR amplification to detect DNA from a patient sample. In addition, it can be used in any flexible cuvette for any processing reaction whatsoever, whether or not nucleic acid is being amplified, provided there is a need to close off an access port prior to doing reactions. .

The preferred method of amplification of the nucleic acid is PCR amplification, the details of which are set forth in the aforesaid EPA publication.

The prior art form of the cuvette set forth in said EPA publication can be briefly summarized as follows. (Further details are found in that publication, and those are expressly incorporated herein by reference).

Figure 1:
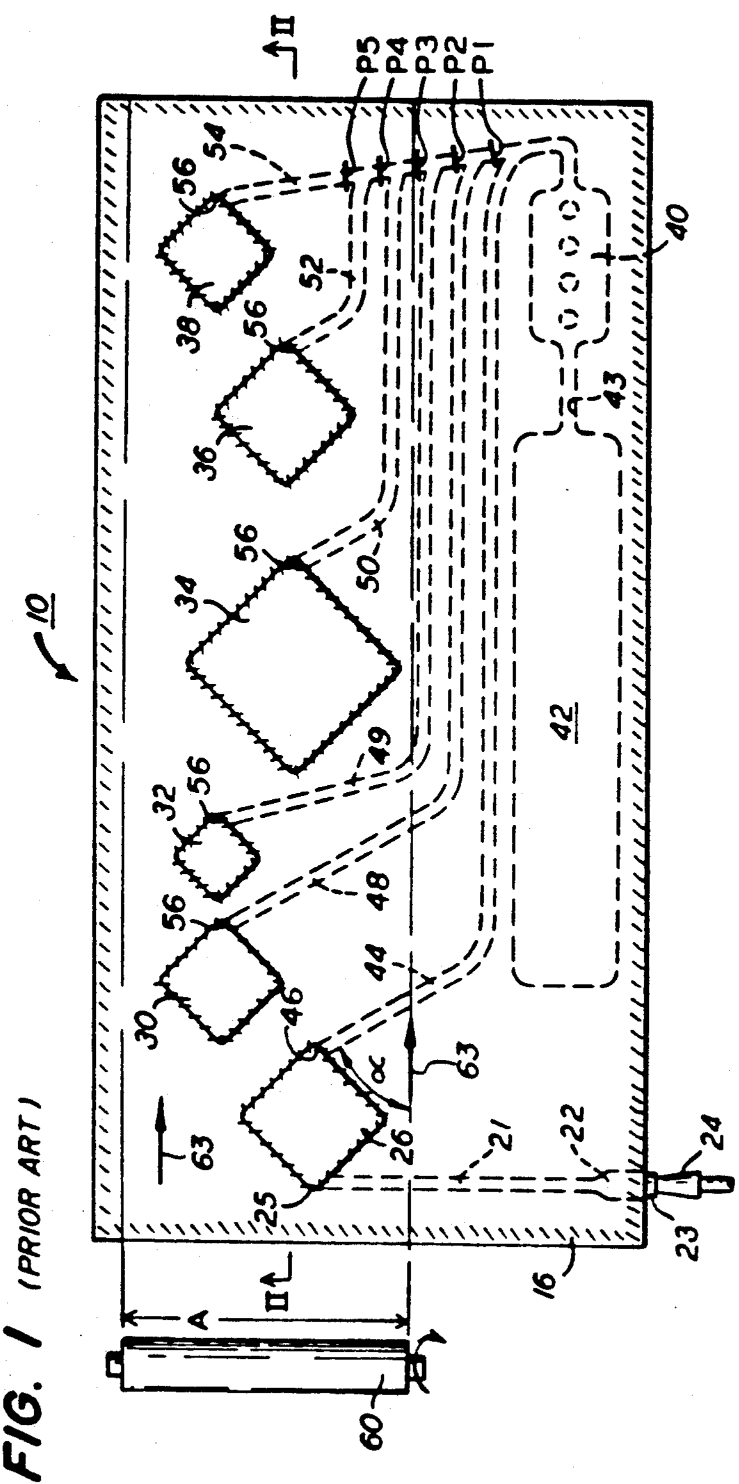
FIG. 1 is a plan view of a cuvette constructed in accord with the prior art.

The cuvette 10 features flexible compartments, FIG. 1, that cooperate with an external pressurizing means 60, such as a pressure roller. More particularly, cuvette 10 comprises two relatively thin sheets 12, 14 formed such as by molding to mate together with pockets or compartments and connecting passageways protruding from the plane of the contacting sheets, FIG. 2. The sheets are secured together at least along their outer periphery 16, and preferably at all points surrounding compartments or passageways, such as by heat- and/or ultrasonic pressure-sealing. A heat-activatable adhesive such as ethylene vinyl acetate is useful for such joining operation. A liquid injection access port 22 is the exception to the sealed periphery 16, for use with a mating pipette 24. Such port 22 optionally includes a rigid rim 23, FIG. 1, extending into it, within which a pipette 24 seats.

Figure 2:
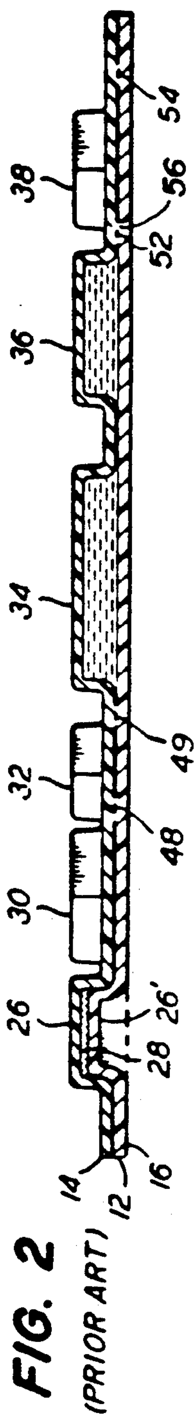
FIG. 2 is a section view taken generally along the line II—II of FIG. 1.

The compartments are as follows: compartment 26 is the reaction compartment, and optionally has the amplifying reagents 28 pre-incorporated therein, FIG. 2, in liquid or dried form. Compartment 30, FIG. 1, is a storage compartment for the first wash compartment containing wash water as a pre-incorporated reagent. Compartment 32 is a storage compartment containing at least one of the detection materials pre-incorporated therein. A biotinylated primer having at one end a complementary nucleotide for attachment to the amplified DNA is placed in compartment 26, whereas compartment 32 stores a signal generating moiety, for example, avidin bound to the horseradish peroxidase discussed above. Storage compartment 34 is a second wash-containing storage compartment, which preferably has a much larger volume than the volume of storage compartment 32. Storage compartment 36 has pre-incorporated therein, the remaining detection reagents, namely a peroxide and a leuco dye, for example 2-(4-hydroxy-3,5- dimethoxyphenyl)-4,5-bis (4-methoxyphenyl)imidazole, preferably in combination with poly(viny pyrrolidone) as a stabilizer. Storage compartment 38 has pre-incorporated therein a stop solution to prevent too much leuco dye from converting to the dye, for example, a solution of sodium azide.

Finally, compartment 40 is the detection site, and compartment 42 is the waste compartment, preferably initially deflated to provide for expansion as liquid is forced into it. Compartment 42 connects to compartment 40 via passageway 43. Optionally, a one-way check valve (not shown) can be included in passageway 43, FIG. 1, to prevent waste liquid from backwashing into compartment 40, thus creating undesirable background color.

The interconnections are as follows: passageway 21 connects injection port 22 with compartment 26, passageway 44 connects reaction compartment 26 with detection compartment 40, except that a temporary seal is provided at 46 to keep introduced DNA in compartment 26 until pressure is generated by roller 60. Optionally, a temporary seal can also be applied at 25 across passageway 21 to hold in the amplifying reagents. Passageway 48 connects compartment 30, passageway 49 connects compartment 32, passageway 50 connects compartment 34, passageway 52 connects compartment 36 and passageway 54 connects compartment 38, all with detection compartment 40, again each preferably with a temporary seal 56, FIG. 2, interrupting flow out of the respective compartment until roller 60 breaks the seal. Passageway 54 serves as the trunk line to which the others (48, 49, 50 and 52) are joined.

The compartments are deliberately positioned, FIG. 1, so that each one will empty into compartment 40 in the proper sequence as roller 60 advances along path A in the direction of arrows 63.

As noted above, care must be taken after the injection of patient sample, to seal off access port 22, as otherwise this becomes a path of leakage.

Figure 3:
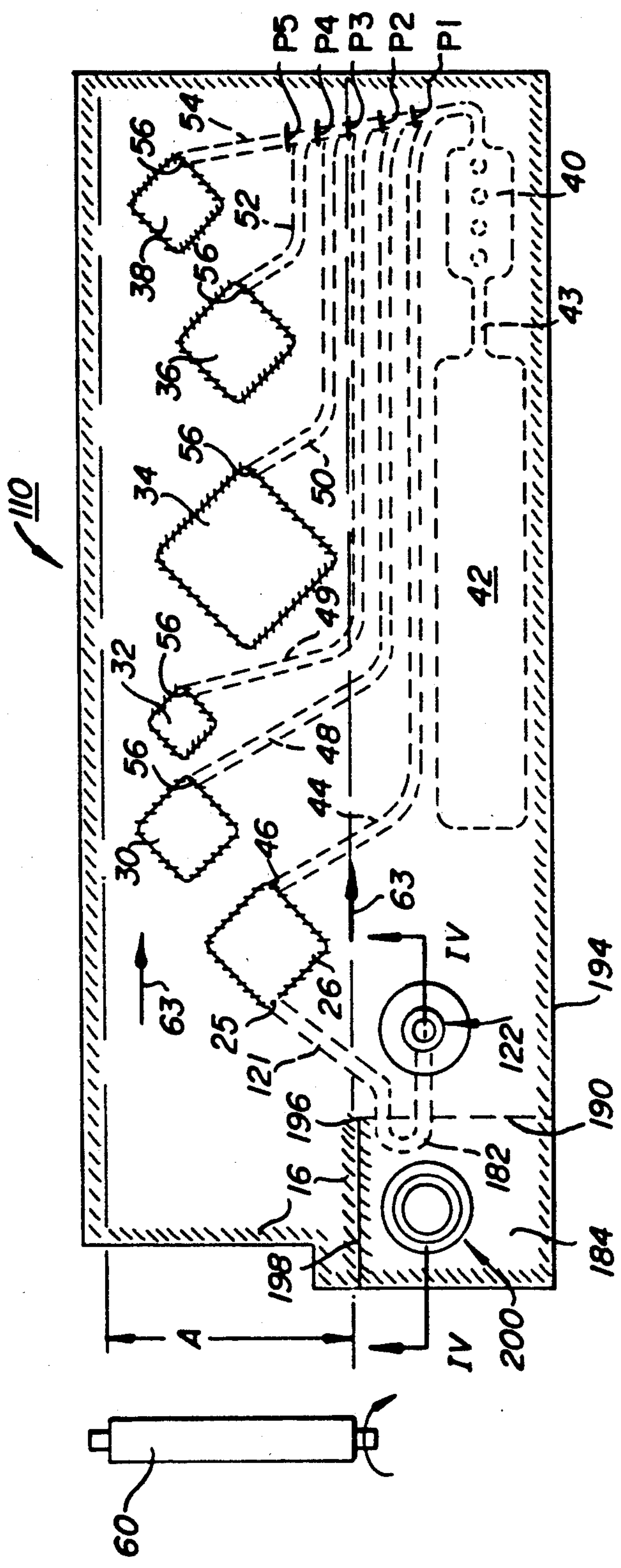
FIG. 3 is a plan view similar to that of FIG. 1, but of the cuvette of the invention.
Figure 4:
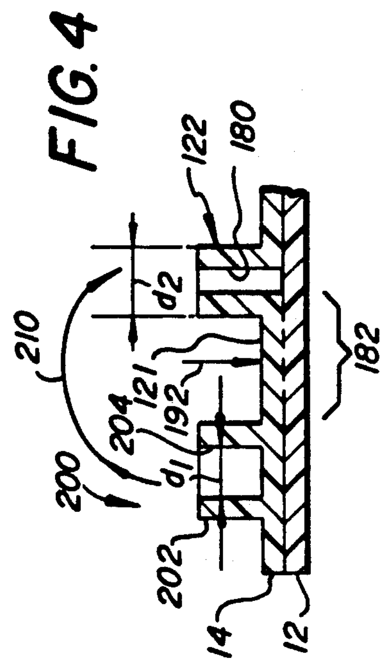
FIG. 4 is a fragmentary section view taken generally along the line IV—IV of FIG. 3.
Figure 5:
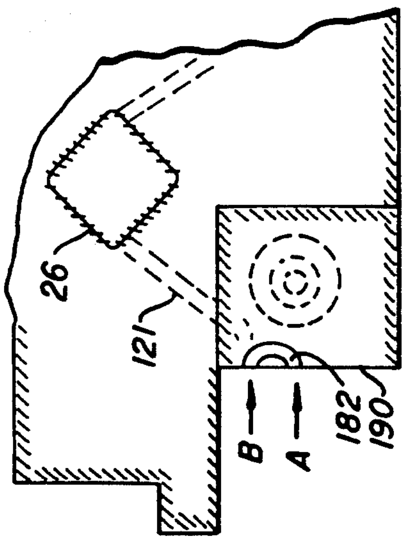
FIG. 5 is a fragmentary plan view similar to that of FIG. 3, showing the cover in place on the access port.

In accord with the invention, the problem with sealing the cuvette of the prior art, and specifically, the access port, is solved as follows (FIGS. 3–5). (In this description, parts identical to those previously described bear the same reference numeral, and those that are similar have the same reference numeral with "100" added). Thus, cuvette 110 comprises a bottom sheet 12 and a top sheet 14, FIG. 4, sealed together generally as discussed for the prior art embodiment. Compartments 26, 30, 32, 34, 36, 38, 40 and 42 are provided, along with their interconnecting passageways 43, 44, 48, 49, 50, 52 and 54, as previously described. Temporary seals are formed at 46 and 56.

However, access port 122, FIGS. 3 and 4, comprises a raised boss on sheet 14 having a central aperture 180 that fluidly connects to passageway 121 left unsealed in the seal between sheets 12 and 14. Passageway 121 extends from port 122 and aperture 180 first away from the reaction compartment 26, along portion 182, and then it doubles back to that reaction compartment. Portion 182 extends into a closure portion 184 of the cuvette that is joined to the remainder of the cuvette only at a hinge line 190, FIG. 3, identified in FIG. 4 by arrow 192. Hence, hinge line 190 cuts across portion 182 of passageway 121 twice. Hinge line 190 extends from an outside edge 194 of cuvette 110, FIG. 3, to an end 196 where it joins a cut portion comprising a line of severance 198 extending completely through sheets 12 and 14 to isolate cover portion 184 except for hinge line 190. (Line of severance 198 is heat-sealed at 16, just as the rest of the periphery of the cuvette is sealed). ·

Portion 184 also includes a closure or cap means 200 projecting upward from sheet 14. Preferably, such means comprise a boss 202 having an aperture 204 that is closed off at its bottom by sheet 14, FIG. 4. Given an outside diameter $d_2$ for port 122, the inside diameter $d_1$ of aperture 204 is selected to provide a friction fit of closure means 200 on port 122. However, this friction fit is not necessarily a seal, as will become apparent.

To seal off passageway 121 after patient sample is injected into compartment 26, closure portion 184 is bent about hinge line 192, FIG. 4, to cause closure means 200 to engage and cover the boss of port 122. (The heights of port 122 and boss 202 are exaggerated in FIG. 4 for clarity. In reality they are reduced sufficiently to allow such connection.) This bending acts to pinch sheets 12 and 14 together across portion 182 of passageway 21, at two locations A and B, FIG. 5, thus sealing off that passageway against leakage. The friction fit of closure means 200 is provided on port 122 to ensure that, once covered, port 122 remains so covered. Other known alternative closure mechanisms can be used to keep closure means 200 covering port 122, for the duration of the test, or permanently if desired.

After sealing off passageway 121, roller 60, FIG. 3, can be passed over the non-cover portions of the cuvette to cause sequential release of the contents of the various compartments. Since only the cover portion of the cuvette is bent to seal off passageway 121, the roller does not have to press against access port 122 and its cover. Alternatively, not shown, cuvette 110 can be positioned between two plates provided with opposed pistons that press against the compartments to burst them in sequence.

Figure 6:
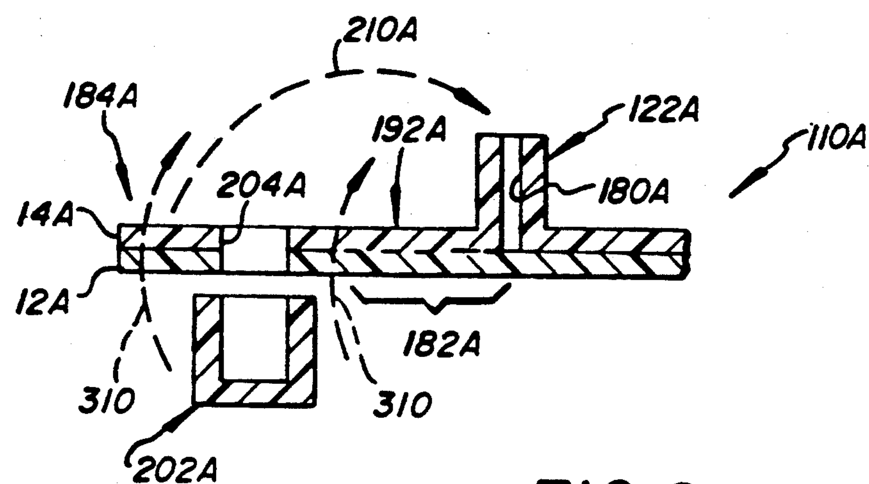
FIG. 6 is a section view similar to that of FIG. 4, but of another embodiment of the invention.

It is not necessary that the cap be integral with the rest of the pouch, as that can be slipped over the access port separately, as shown in FIG. 6. Parts similar to those previous described bear the same reference numeral to which the distinguishing suffix "A" is appended.

Thus, cuvette 110A has an access port 122A with an aperture 180A that feeds to a passageway portion 182A that passes through a hinge line, arrow 192A, around which closure portion 184A is folded to pinch closed passageway portion 182A. However, in this case, the closure means comprises, in portion 184A, an aperture 204A, which extends completely through sheets 12A and 14A. The cover boss 202A is a cap piece separate from portion 184A. After aperture 204A is slipped around port 122A, arrow 210A, cover 202A is also inserted over port 122A, arrows 310, thus completing the closure. However, cap 202A, as before, is not the means that seals off passageway portion 182A, since that occurs from the pinching of that portion at 192A. Rather, cap 202A serves to ensure that portion 184A stays in place on port 122A to maintain that pinching of portion 182A.

Figure 7:
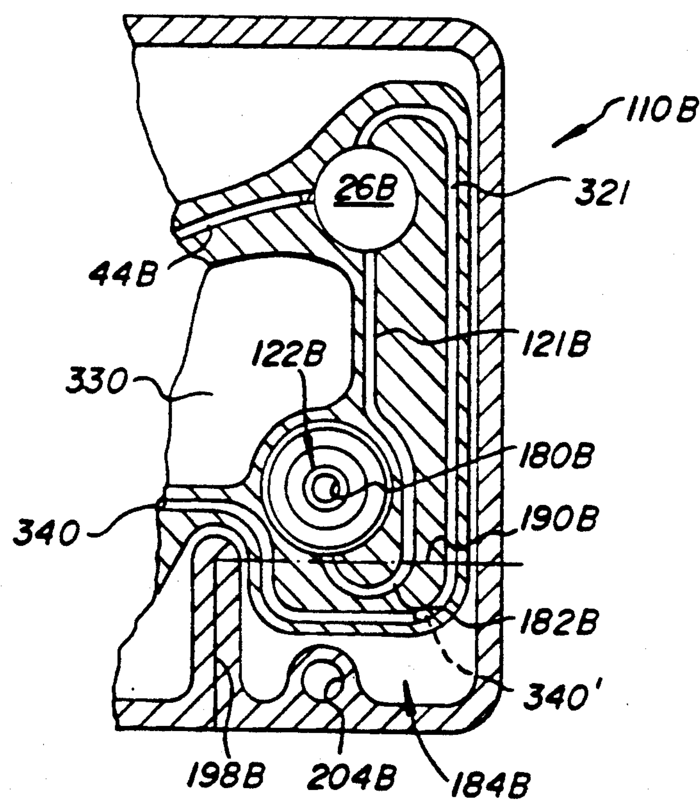
FIG. 7 is a fragmentary plan view similar to that of FIG. 3, but illustrating yet another alternative embodiment.

An additional option of the invention is to include an air vent passageway from the chamber into which the patient sample is injected, FIG. 7. Parts similar to those previously described bear the same reference numeral, to which the distinguishing suffix "B" is appended.

Thus, FIG. 7, cuvette 110B includes an access port 122B wherein an aperture 180B connects to a feed passageway 121B that connects to a reaction compartment 26B having a sealed outlet passageway 44B. (Hatched portions represent the portions of the cuvette wherein the two opposed sheets are sealed together.) Closure portion 184B with aperture 204B features a hinge line 190B and a cut line 198B that allows closure aperture 204B to slip over portion 122B when portion 184B is folded about line 190B, as described heretofore. Because hinge line 190B passes through portion 182B of passageway 121B, the folding of portion 184B acts to pinch shut passageway 121B.

In addition, an air vent passageway 321 extends from compartment 26B back to a suitable vent aperture on the exterior surface 330 of pouch 110B, for example an aperture 340, or to the waste chamber (not shown here). Passageway 321 also extends across hinge line 190B so as to be pinched shut when the access passageway 121B is sealed. Although passageway 321 is shown as crossing hinge line 190B twice, it could cross only once, by locating aperture 340 at dotted position 340', for example.

It is not essential that the hinge line used to seal the sample injection passageway must cross that passageway twice. The cuvette can be constructed so that it crosses it once, FIG. 8. Parts similar to those previously described bear the same reference numeral, to which the distinguishing suffix "C" has been appended.

Thus, cuvette 110C is formed from two opposing sheets by sealing them together to leave a reaction compartment 26C connected to access port 122C and to other compartments via passageways 121C and 44C, as previously described. Closure portion 184C is also formed by a line of severance 198C and a hinge line 190C, also as previously described, so that port 122C can be inserted into a closure means 200C comprising a raised boss 202C also as previously described. However, the positions of port 122C and closure means 200C have been reversed, so that passageway 121C is crossed by hinge line 190C only once.

Figure 8:
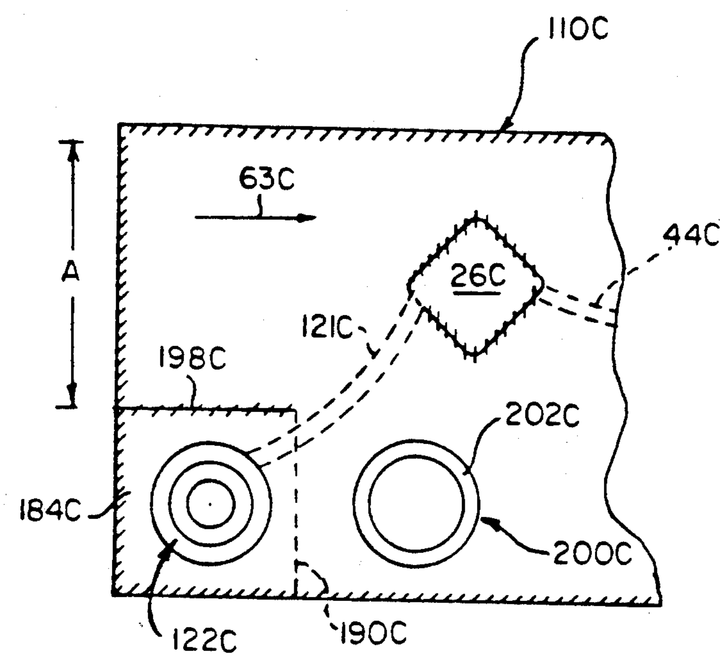
FIG. 8 is a fragmentary plan view similar to that of FIG. 1, but illustrating a still further alternative embodiment.

For the corner fold embodiment of FIG. 8, it is not necessary that a portion of the cuvette be especially modified to allow hinging and folding to occur. Such modification, such as severance of the cuvette at an angle to the hinge line, can be eliminated if the pouch is constructed as per FIGS. 9-10. Parts similar to those previously described bear the same reference numerals, to which the distinguishing suffix "D" is appended.

Thus, cuvette 110D has an access port 122D that feeds into a passageway 121D extending to reaction compartment 26D, with hinge line 190D crossing passageway 121D at at least one location, as described heretofore. Capping of the access port to hold it in the folded-over, pinched-off condition, is provided, as before, by dead-end closure cap means 200D, to ensure that the pinching of passageway 121D by the folding at arrow 192D, FIG. 10, remains for the duration of the assay. However, unlike the previous embodiments, hinge line 190D extends at an angle alpha and gamma to the two sides of the cuvette, rather than parallel to one of the sides, thereby allowing the hinging at line 190D to occur without having to sever the cuvette along a line intersecting the hinge line.

Figure 9:
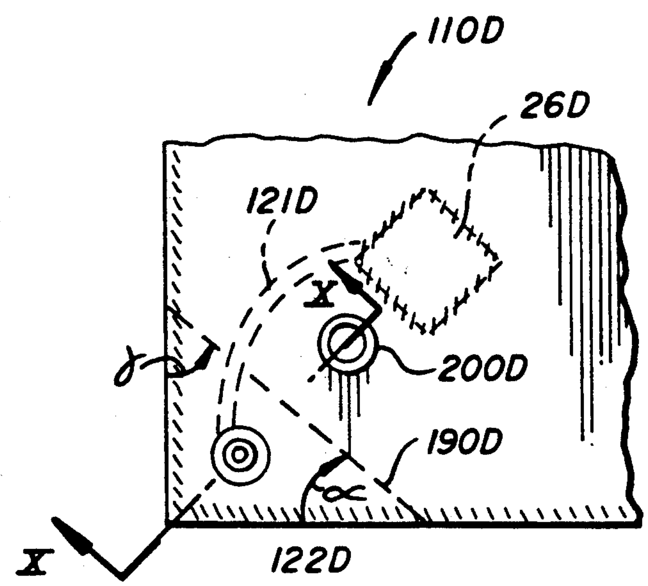
FIG. 9 is a fragmentary plan view similar to that of FIG. 8, of still a further embodiment.
Figure 10:
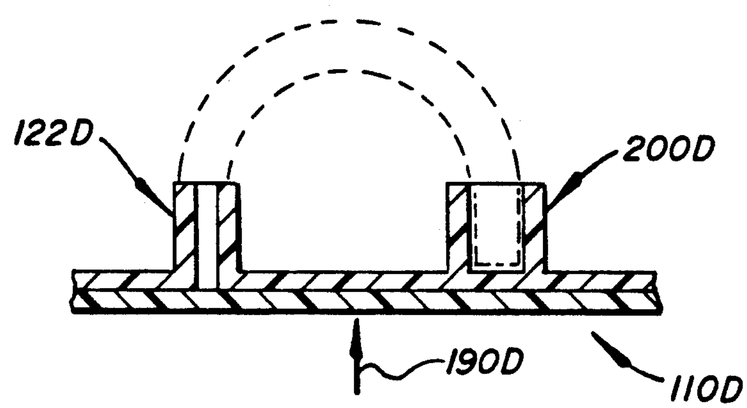
FIG. 10 is a fragmentary section view taken along the line X—X of FIG. 9.
Figure 11:
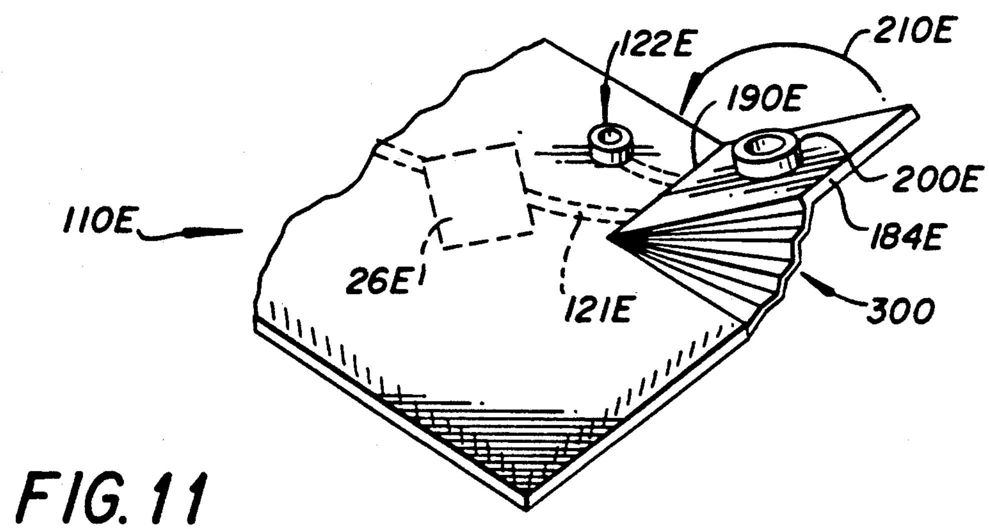
FIG. 11 is a fragmentary isometric view of a cuvette showing yet another embodiment.

If for some reason, hinge line 190 cannot extend across a corner as shown in FIGS. 9 and 10, other ways can be provided to allow hinging and folding to occur, as shown in FIG. 11, besides by severing the cuvette. Parts similar to those previously described bear the same reference numeral, to which the distinguishing suffix "E" is appended. Thus, cuvette 110E comprises an access port 122E for feeding sample via a passageway 121E to reaction compartment 26E and beyond, as described heretofore, with a hinge line 190E crossing passageway 121E (here, at two locations) to pinch it off when portion 184E is folded over to allow capping shoulder 200E to friction fit over port 122E. However, to allow the folding over of portion 184E at line 190E, no severance of the cuvette is needed. Instead, portion 184E is joined to the rest of the cuvette by a flexible fan-fold 300, which allows portion 184E to be coplanar with the rest of the cuvette, or folded over in the direction of arrow 210E.

Still further, when fastening the folded-over portion in place to maintain the pinching of the passageway, it is not necessary that the friction-fitting cap engage the access port. Instead, it can engage a dead-end boss provided for that purpose, FIG. 12. Parts similar to those previously described bear the same reference numeral to which the distinguishing suffix "F" is appended.

Figure 12:
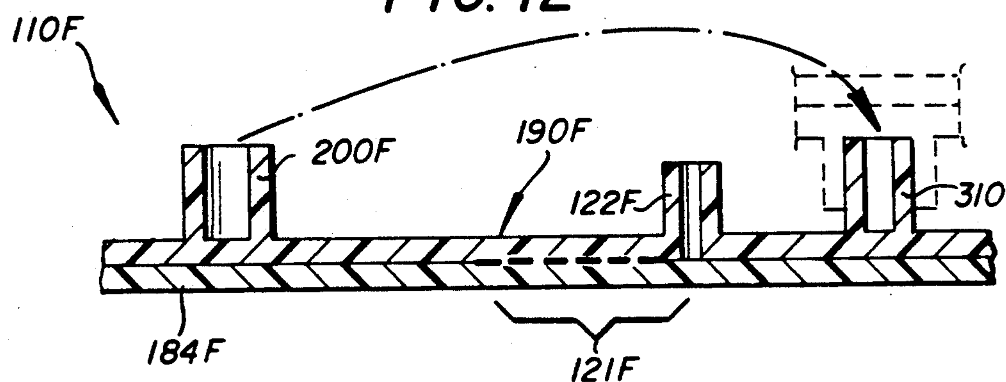
FIG. 12 is a section view similar to that of FIG. 10, of still another embodiment.

Thus, FIG. 12, cuvette 110F is provided exactly as before, with a hinge line 190F crossing over passageway 121F (shown as a dotted line) that extends from access port 122F to the subsequent compartment(s) (not shown). Also as before, a cap 200F is provided on fold-over portion 184F to lock the latter to the rest of the cuvette with passageway 121F pinched off. However, unlike the previous embodiments, a dead-end boss 310 is provided separate from access port 122F, and it is this boss over which cap 200F is friction-forced to hold portion 184F in its folded-over configuration (shown in phantom).

Still further, it is not necessary that the hinge line, and subsequent pinching off, occur only across the passageway leading from the access port to the reaction compartment. It can also be used to pinch off unwanted flow away from the reaction or any other compartment during heating, downstream towards the detection compartment or site, FIGS. 13 and 14. Parts similar to those previously described bear the same reference numeral, to which the distinguishing suffix "G" is appended.

Figure 13:
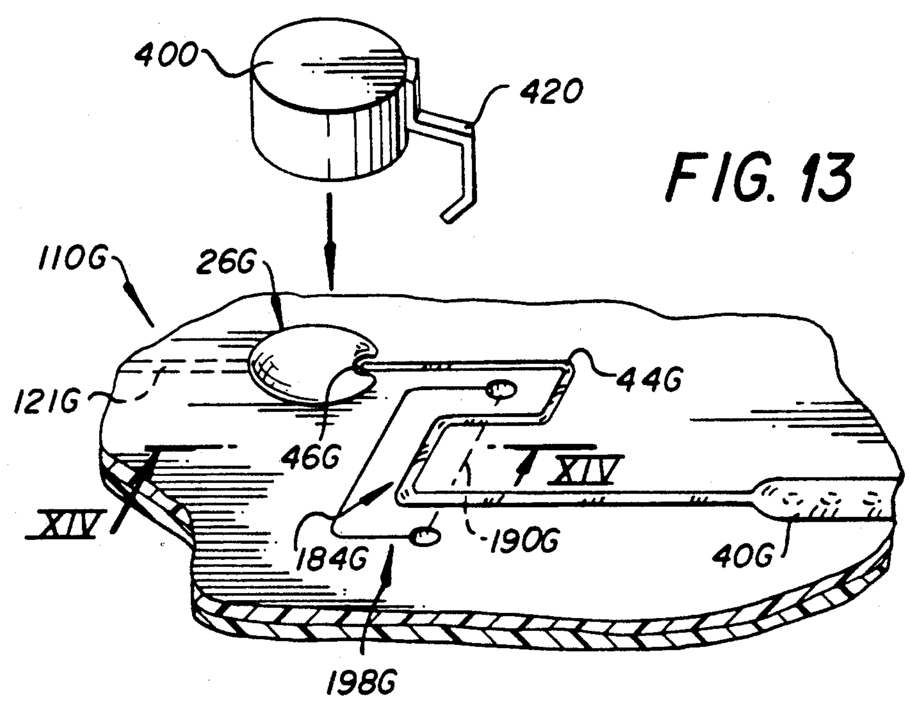
FIG. 13 is a fragmentary isometric view of yet another embodiment, in association with a heater for the cuvette, shown here raised.

Thus, FIG. 13, cuvette 110G comprises the various compartments as described in previous embodiments, and connecting passageways. However, for each compartment that has to be heated, such as reaction compartment 26G, there is a temporary seal 46G that is intended to not leak during heating until a bursting pressure is applied. That seal is located opposite to any incoming passageway such as passageway 121G (none being present for reagent compartments). The difficulty is that, under some conditions, seal 46G can leak during heating, allowing liquid (patient sample or reagent, depending on the compartment involved) to prematurely pass on to detection sites in detection compartment 40G.

To avoid this, the hinge line of the invention, line 190G, is formed to cross the passageway extending downstream of the burstable seal — passageway 44G in the case of reaction compartment 26G. Furthermore, cuvette 110G is severed along line 198G to form a fold-over portion 184G located in the interior of the cuvette.

Figure 14:
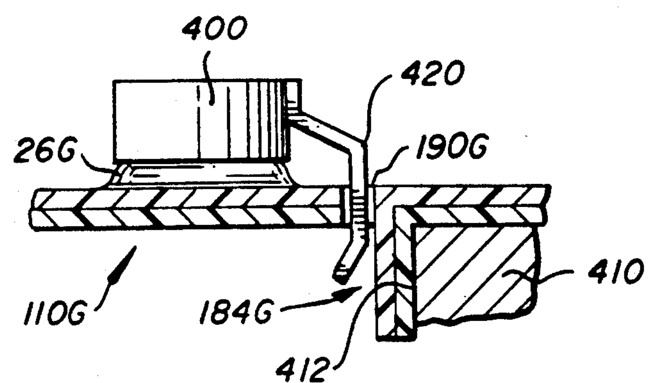
FIG. 14 is a fragmentary elevational view in section, taken along the line XIV—XIV of FIG. 13 but with the heater lowered into contact.

The operation is shown in FIG. 14. Prior to placing a heater 400 in contact with the compartment to be heated, e.g., compartment 26G, a support 410 with a straight edge 412 is place aligned with hinge line 190G. When heater 400 is lowered into contact, a pusher finger 420 on the heater folds portion 184G along the hinge line, pinching off the passageway downstream of the seal, thus preventing liquid from prematurely entering the next compartment (e.g., compartment 40G), even if seal 46G should leak. In this operation, unlike the pinching off of the passageway from the access port, the pinching is temporary only and is released following heating to allow flow to occur once again (when the upstream compartment is deliberately burst immediately following the heating.)

Figure 15:
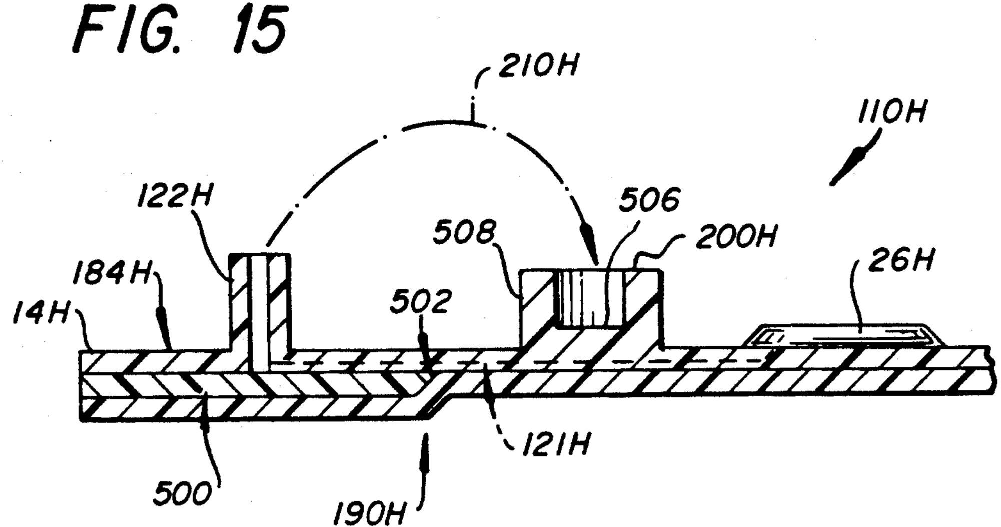
FIG. 15 is a fragmentary section view similar to that of FIG. 10, but of still another embodiment.
Figure 17:
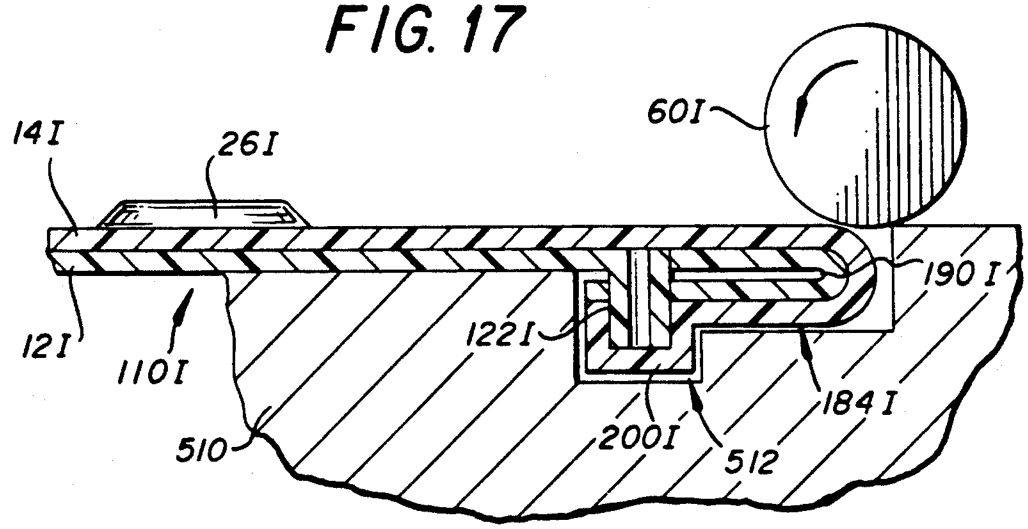
FIG. 17 is a fragmentary section view similar to that of FIG. 15, but of still another embodiment, wherein pinching off of flow has already been achieved.
Figure 16:
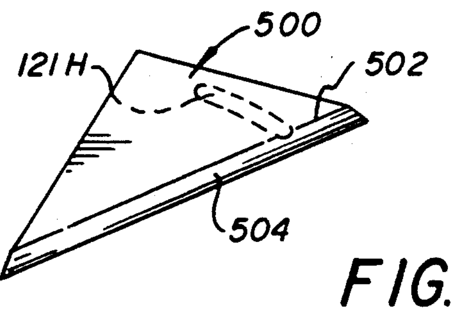
FIG. 16 is an isometric view of the piece 500 shown in FIG. 15.

The pinching shut of the passageway can be enhanced in several ways, by either the cuvette itself, or the processing apparatus. These are illustrated in FIGS. 15-17. Parts similar to those previously described bear the same reference numerals, to which the distinguishing suffixes "H"and "I" are appended, respectively.

Thus, FIG. 15, a corner fold such as is shown in FIGS. 9 and 10 can be enhanced by an inflexible fold bar disposed adjacent to the hinge line, so that as the corner is folded over, the edge of the fold bar acts to further pinch shut the passageway. More specifically, device 110H is formed by opposing sheets with a passageway 121H leading from inlet port 122H to a reaction compartment 26H, and a cap means 200H is provided to cover port 122H when folding occurs about hinge line 190H, arrow 210H, as is described previously for the embodiment of FIGS. 9 and 10. Additionally, a relatively solid, inflexible member or piece of plastic 500 is inserted in corner portion 184H, so that one of its edges 502 is beveled at 504 to form a relatively sharp edge, FIG. 16. Passageway 121H in turn is formed over piece 500, either by dimpling sheet 14H to preform a channel, or by grooving piece 500 as suggested by the phantom lines, FIG. 16.

When portion 184H is folded over hinge line 190H, arrow 210H, piece 500 acts to enhance the pinching off of passageway 121H at line 190H, as will be readily appreciated.

Alternatively, not shown, piece 500 can be replaced by an inflexible member such as a bar placed on the exterior of the pouch, rather than in the interior, to extend with an edge adjacent the fold line.

FIG. 15 also illustrates that the cap means can have thicknesses in excess of the thickness of the single sheet 14H. E.g., base 506 of cap 200H is thicker than the thickness of sheet 14H, as are the sidewalls 508. This is readily achieved by manufacturing cap 200H as a separate component and then adhesively securing it to sheet 14H in the position shown.

A similar increase can be achieved in the sidewalls of port 122H.

As is noted above, an external pressure member such as a roller is used to burst at least the reaction compartment after suitable reactions occur. This roller can also be useful in enhancing the pinching off of the passageway, FIG. 17. In such an embodiment, cuvette 110I features an inlet or access port 122I, a cap means 200I, a passageway (not shown) extending between sheets 14I and 12I to a burstable compartment 26I, and a hinge line 190I about which corner portion 184I can be folded to pinch off the passageway, as described heretofore. (Unlike previous embodiments, port 122I and cap means 200I project from the cuvette in a direction opposite to the projection of compartment 26I, as a further option.) Most preferably, cuvette 110I is processed on a support 510 having a recess 512 that accommodates the protrusion of port 122I and cap means 200I, and a roller 60I used to burst compartment 26I is also used to enhance the pinching off of flow in the passageway by creasing with pressure, the hinge line 190I. Once the creasing by roller 60I is achieved, it can be rolled on to burst compartment 26I since the crease at hinge line 190I is effective to hold the passageway pinched off. This embodiment can be used with or without the enhancer shown in FIGS. 15-16.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In a flexible cuvette defined by opposed flexible sheets sealed together to contain at least one temporarily sealed chamber containing a reagent, and a patient sample access port constructed to be closed after sample injection, said port being fluidly connected to said at least one chamber of said cuvette by a passageway;

the improvement wherein said cuvette further includes on a portion thereof, closure means for frictionally engaging said port, said portion being integrally connected to the rest of said cuvette about a hinge line, a portion of said hinge line being constructed to pass through said passageway adjacent to said port, so that bending of said portion along said hinge line to engage said port with said closure means causes said opposed sheets of said cuvette to pinch and seal said passageway closed.

2. A cuvette as defined in claim 1, wherein said closure means includes a cap that is integral with said cuvette.

3. A cuvette as defined in claim 1, wherein said closure means is a corner portion of said cuvette, and further including a cut portion extending along a line from said hinge line and separating said closure portion from the remainder of said cuvette except at said hinge line, so that said closure means is easily bent about said hinge line to pinch closed said passageway.

4. A cuvette as defined in claim 1, 2 or 3, wherein said reagent is suitable for amplifying or detecting DNA, said cuvette being completely sealed against leakage once said port is closed off with said closure means.

5. A cuvette as defined in claim 1, 2 or 3, wherein said hinge line passes through said passageway twice.

6. A cuvette as defined in claim 1, and further including an air vent passageway extending from said chamber of said cuvette to the exterior of said cuvette, a portion of said air vent passageway extending through said hinge line, so that said air vent passageway is sealed shut when said closure means is bent to engage said port.

7. A method for sealing off the access port of a flexible cuvette connected to at least one internal compartment by a passageway, the method comprising the steps of a) providing closure means on a portion of said cuvette joined to said cuvette along a hinge line that is located to intersect said passageway, said closure means being constructed to friction-fit with said access port, and b) bending said closure means about said hinge line until said closure means frictionally engages said access port and said passageway is pinched off at said hinge line against any further flow.

* * * * *